United States Patent [19]

Akkerman et al.

[11] Patent Number: 4,473,576
[45] Date of Patent: Sep. 25, 1984

[54] ANALGESIC 9,9-DIMETHYLBENZOMORPHANES

[75] Inventors: Antony M. Akkerman, Amsterdam; Hermanus C. C. K. van Bakel, Montfoort, both of Netherlands

[73] Assignee: ACF Chemiefarma NV, Maarssen, Netherlands

[21] Appl. No.: 546,849

[22] Filed: Oct. 31, 1983

Related U.S. Application Data

[63] Continuation of Ser. No. 409,317, Aug. 18, 1982, abandoned, which is a continuation of Ser. No. 329,347, Dec. 10, 1981, abandoned, which is a continuation of Ser. No. 155,196, Jun. 2, 1980, abandoned, which is a continuation of Ser. No. 31,780, Apr. 20, 1979, abandoned.

[30] Foreign Application Priority Data

Apr. 26, 1978 [NL] Netherlands ......................... 7804509

[51] Int. Cl.³ ................. A61K 31/445; C07D 221/26; C07D 401/04; C07D 405/06
[52] U.S. Cl. ....................................... 424/267; 546/97
[58] Field of Search .......................... 546/97; 424/267

[56] References Cited

U.S. PATENT DOCUMENTS

| 3,320,265 | 5/1967 | Clarke | 546/97 |
| 3,513,169 | 5/1970 | Robinson et al. | 546/97 |
| 4,020,164 | 4/1977 | Rahtz et al. | 546/97 X |
| 4,087,532 | 5/1978 | Merz et al. | 546/97 X |

FOREIGN PATENT DOCUMENTS

0006449  1/1980  European Pat. Off. .............. 546/97

OTHER PUBLICATIONS

Rahtz, D. et al., *Eur. J. Med. Chem.-Chim. Ther.,* 12, 271, (1977).

*Primary Examiner*—Richard A. Schwartz
*Attorney, Agent, or Firm*—Gerald D. Sharkin; Robert S. Honor; Thomas O. McGovern

[57] ABSTRACT

9,9-Dimethyl-6,7-benzomorphan derivatives having an oxygen-containing substituent on the nitrogen atom, optionally an alkyl or phenyl 5-substituent and optionally a hydroxy, alkoxy or acyloxy 2'-substituent have analgetic and/or morphine-antagonist properties.

28 Claims, No Drawings

ANALGESIC 9,9-DIMETHYLBENZOMORPHANES

This is a continuation of application Ser. No. 409,317, filed Aug. 18, 1982, now abandoned, which in turn is a continuation of application Ser. No. 329,347, filed Dec. 10, 1981, now abandoned, which in turn is a continuation of application Ser. No. 155,196, filed June 2, 1980, now abandoned, which in turn is a continuation of application Ser. No. 31,780, filed Apr. 20, 1979, now abandoned.

This invention relates to 6,7-benzomorphan derivatives. In Dutch Patent Application No. 73.09158 6,7-benzomorphans of formula II

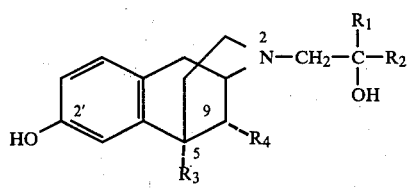

are described, in which $R_1$ is hydrogen, methyl or ethyl, $R_2$ is methyl or ethyl and $R_3$ and $R_4$ are alkyl substituents. According to the description, the compounds possess analgetic activity.

In Eur. J. Med. Chem. 12, 271-278 (1977) 2-hydroxyalkyl-6,7-benzomorphan derivatives are described, which have analgetic, morphine-antagonistic and muscle-relaxing activity. The compounds are 5-methyl, as well as 9-monomethyl substituted.

In Dutch Patent Application No. 75.02724 2-tetrahydrofurfuryl-benzomorphans are described having a 5-methyl, -ethyl or -propyl substituent and 0, 1 or 2 9-lower alkyl substituents.

In Dutch Patent Application No. 76.01924 analogous 2-tetrahydrofurfuryl benzomorphans are described, which however are substituted with two 9-lower alkyl groups and which are unsubstituted in position 5.

2-Tetrahydrofurfuryl-6,7-benzomorphans having one 9-methyl and one 5-methyl or -phenyl substituent and which possess analgetic activity are described in Dutch Patent Application No. 75.09249.

In Dutch Patent Application No. 71.04557 2-benzoylalkyl-benzomorphans are disclosed which are prepared by oxidation of the corresponding hydroxy substituted phenylalkyl compounds. No pharmacological activity was described.

British Patent No. 1,299,669 discloses 9,9-dialkyl-6,7-benzomorphans, substituted in the 5-position and optionally in the 2- and/or 2'-positions.

However, all 6,7-benzomorphans mentioned in the cited literature which have hydroxy in the 2-substituent, have a tertiary carbon atom in position 9, that is to say a carbon atom with only one alkyl substituent.

It has now been found that 6,7-benzomorphan derivatives with a quaternary carbon atom in position 9 and having a substituent in position 2 containing at least one oxygen atom, possess unexpected pharmacological, in particular analgetic and/or morphine-antagonistic, activity.

The present invention provides compounds of formula I

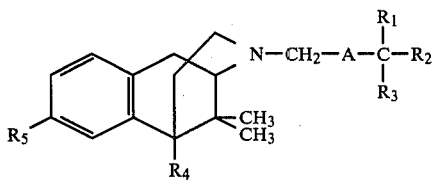

in which
A is a direct bond or —CH$_2$—,
$R_1$ is hydrogen, C$_{1-3}$alkyl, C$_{2-3}$alkenyl, C$_{2-3}$alkynyl, C$_{1-2}$alkoxy C$_{1-2}$alkyl or C$_{3-6}$ cycloalkyl,
$R_2$ is hydrogen or C$_{1-3}$alkyl, or
$R_1$ and $R_2$, together with the carbon atom to which they are attached, form a C$_{3-6}$cycloalkyl group or a 4 to 6-membered heterocycloalkyl group containing one oxygen atom as the sole hetero atom,
$R_3$ is hydroxy, C$_{1-4}$alkoxy, C$_{2-4}$alkenyloxy, or R$_6$COO- in which R$_6$ is hydrogen, C$_{1-3}$alkyl, phenyl or benzyl
$R_4$ is hydrogen, C$_{1-4}$alkyl or phenyl, and
$R_5$ is hydrogen, hydroxy, C$_{1-3}$alkoxy or R$_7$COO- where R$_7$ is hydrogen, C$_{1-3}$alkyl, phenyl, benzyl, phenethyl or 3-pyridyl.

Generally the compounds in which the oxygen atom of the nitrogen substituent is bound to the carbon atom situated in the β-position in relation to the nitrogen atom of the ring, are preferred. A is therefore preferably a direct bond.

Where $R_1$ is C$_{1-3}$alkyl, it is preferably methyl or ethyl, more preferably methyl. Where it is C$_{2-3}$alkynyl it is preferably ethynyl: where it is alkoxyalkyl it is preferably methoxymethyl, and where it is cycloalkyl it is preferably cyclopropyl. $R_1$ is preferably $R_1'$ where $R_1'$ is hydrogen, alkyl or alkenyl; more preferably it is $R_1''$ where $R_1''$ is hydrogen, methyl, ethyl or ethynyl.

Where $R_2$ is C$_{1-3}$alkyl it is preferably methyl or ethyl. $R_2$ is preferably $R_2'$ where $R_2'$ is hydrogen, methyl or ethyl.

Where $R_1$ and $R_2$ together with the carbon atom to which they are attached form a cycloalkyl ring, this is preferably cyclopropyl, cyclobutyl or cyclopentyl, more preferably cyclopropyl or cyclobutyl, particularly cyclopropyl. Where they form a heterocyclic ring, this is preferably

A preferred significance of $R_1$ and $R_2$ taken together is —Z— where —Z— is —CH$_2$—CH$_2$, —CH$_2$—$_3$ or —CH$_2$—$_4$, more preferably —Z'— where —Z'— is —CH$_2$—CH$_2$— or —CH$_2$—$_3$, particularly —CH$_2$—CH$_2$—.

$R_3$ as alkoxy is preferably methoxy or ethoxy, and as alkenyloxy is preferably CH$_2$=CH.CH$_2$O—. Where $R_3$ is R$_6$.COO—, R$_6$ is preferably C$_{1-3}$alkyl. Preferably $R_3$ is $R_3'$ where $R_3'$ is hydroxy, alkoxy or acyloxy, more preferably $R_3''$ where $R_3''$ is hydroxy, methoxy, ethoxy, acetoxy, propionyloxy, n-butyryloxy or iso-butyryloxy; still more preferably $R_3'''$, where $R_3'''$ is hydroxy, methoxy or ethoxy; particularly hydroxy.

$R_4$ is preferably $R_4'$ where $R_4'$ is hydrogen, methyl, ethyl, n-propyl or phenyl, more preferably $R_4''$ where $R_4''$ is methyl or ethyl, particularly ethyl.

$R_5$ as alkoxy is preferably methoxy. Where $R_5$ is $R_7COO-$, $R_7$ is preferably methyl, ethyl, benzyl or 3-pyridyl. $R_5$ is preferably $R_5'$ where $R_5'$ is hydroxy, alkoxy or acyloxy, more preferably $R_5''$ where $R_5''$ is hydroxy, methoxy, acetoxy, propionyloxy, benzoyloxy and nicotinoyloxy; particularly hydroxy.

Preferred compounds of formula I are those in which, independently,

A is a direct bond, $R_1$ is $R_1'$, more preferably $R_1''$, $R_2$ is $R_2'$, or $R_1$ and $R_2$ together are $-Z-$, more preferably $-Z'-$, particularly $-CH_2-CH_2-$, $R_3$ is $R_3'$, more preferably $R_3''$, still more preferably $R_3'''$, particularly hydroxy, $R_4$ is $R_4'$, more preferably $R_4''$, particularly ethyl, and $R_5$ is $R_5'$, more preferably $R_5''$, particularly hydroxy.

A particular group of preferred compounds of formula I are those of formula Ia

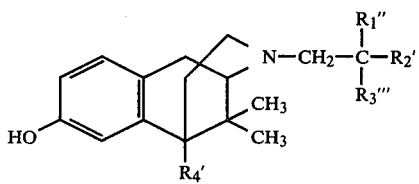

in which $R_1''$, $R_2'$, $R_3'''$ and $R_4'$ are as defined above. More preferred compounds of formula Ia are those of formula Ia'

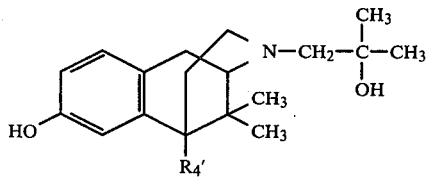

in which $R_4'$ is as defined above.

A further group of preferred compounds of formula I are those of formula Ib

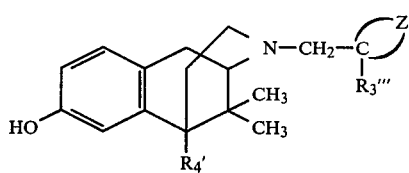

in which Z, $R_3'''$ and $R_4'$ are as defined above, more preferably those in which $R_4'$ is $R_4''$, Z is Z' and $R_3'''$ is hydroxy or methoxy. Particularly preferred are compounds of formula Ib'

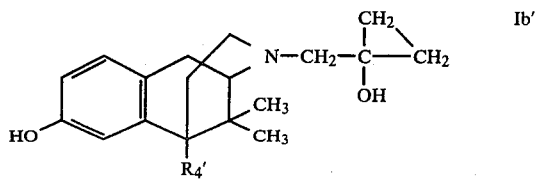

in which $R_4'$ is as defined above.

The compounds of formula I may exist in free base form or in the form of their acid addition salts, for example their salts with mineral acids e.g. hydrochloric, hydrobromic or sulphuric acid, or organic acids, e.g. maleic, oxalic or tartaric acid. The 6,7-benzomorphan structure contains two asymmetric carbon atoms $C_1$ and $C_5$. The imino ethano bridge between $C_1$ and $C_5$ is fixed as a cis-configuration (1,3-diaxial) and therefore only one racemate exists, provided that there are no additional asymmetrical carbon atoms in a side chain. The racemate can be resolved into optical isomers. One or more asymmetric carbon atoms in the N-substituent may give rise to several diastereoisomeric forms.

The compounds of the invention, as represented by formula I, include free base and acid addition salt forms, racemates, separated optical forms and mixtures thereof.

The invention also provides a process for the preparation of compounds of formula I, in which (A) 2-acyl-9,9-dimethyl-6,7-benzomorphan of formula III

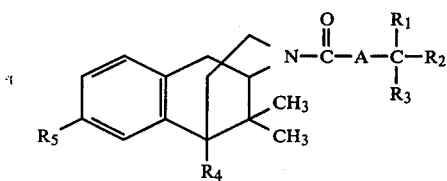

is which A and $R_1-R_5$ are as defined above, is reduced, or (B) a benzomorphan of formula IV

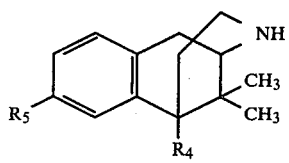

in which $R_4$ and $R_5$ are as defined above, is alkylated with a compound of formula V

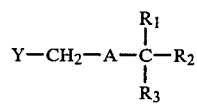

in which A, $R_1$, $R_2$ and $R_3$ are as defined above and Y is a nucleophilic leaving group, particularly chlorine, bromine, iodine, aryl-, alkaryl- or alkylsulphonyloxy, particularly mesyloxy or tosyloxy, or (C) a benzomorphan of formula IV above is reacted with an epoxide of formula VI

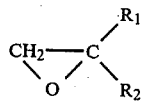

(VI)

in which $R_1$ and $R_2$ are as defined above, to give a compound of formula I in which $R_3$ is hydroxy and A is a direct bond, or (D) a benzomorphan of formula IV above is reacted with a compound of formula VII

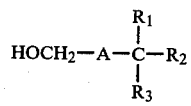

(VII)

in which A, $R_1$, $R_2$ and $R_3$ are as defined above, in the presence of a Raney-nickel catalyst, or (E) a benzomorphan derivative of formula VIII

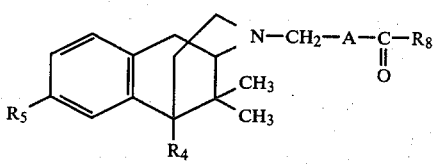

(VIII)

in which A, $R_4$ and $R_5$ are as defined above and $R_8$ is hydrogen, alkyl, cycloalkyl, hydroxy or alkoxy, is reduced to give a compound of formula I in which $R_1$ is hydrogen, alkyl or cycloalkyl, $R_2$ is hydrogen and $R_3$ is hydroxy. If $R_5$ in the compound of formula VIII is acyloxy, this will be reduced to hydroxy; or (F) a compound of formula VIII above is reacted with an organometallic compound $R_9M$ where $R_9$ is alkyl, alkenyl, alkynyl or cycloalkyl and M is a metal atom or metal-containing radical, preferably lithium, —MGI or —MgBr, to give, when $R_8$ is alkyl, a compound of formula I in which $R_1$ is $R_9$, $R_2$ is alkyl and $R_3$ is hydroxy. Reacting a compound of formula VIII in which $R_8$ is alkoxy with $R_9'M$ where $R_9'$ is alkyl, a compound of formula I is obtained in which $R_1=R_2=R_9'$ and $R_3=OH$. Similarly, where $R_8$ in VIII is hydrogen, a compound of formula I is obtained in which $R_1=R_9'$, $R_2=$hydrogen and $R_3=OH$. If $R_5$ in VIII is acyloxy, this will normally be converted to hydroxy, or (G) a compound of formula I in which $R_3$ and/or $R_5$ is hydroxy is alkylated, or (H) a compound of formula I in which $R_3$ and/or $R_5$ is hydroxy is acylated, or (I) a compound of formula I in which $R_3$ and/or $R_5$ is alkoxy, is cleaved to replace the alkoxy group with hydroxy, or (J) a compound of formula I in which $R_3$ and/or $R_5$ is acyloxy is hydrolysed to replace the acyloxy group with hydroxy.

In method A the reduction is suitably carried out using diborane or a complex hydride, such as lithium aluminium hydride. The hydride is added in equivalent amounts or in excess, preferably in quantities up to double the equivalent amounts. The reduction is preferably carried out in an inert solvent, in particular tetrahydrofuran, at a reaction temperature between 0° C. and the boiling point of the solvent.

It must be noted that such reducing agents will also be able to reduce O-acyl groups. In compounds of formula III in which $R_3$ and $R_5$ are acyloxy, these groups usually will be converted to hydroxy groups leading to compounds of formula I in which $R_3$ and $R_5$ are hydroxy.

The compounds of formula III may be prepared for example by acylation of a benzomorphan of formula IV with a compound of formula IX

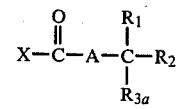

(IX)

in which A, $R_1$ and $R_2$ are as defined above, $R_{3a}$ is as $R_3$ except that it may not be hydroxy, and X is halogen or

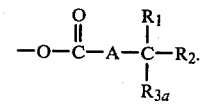

The acylation of the benzomorphan of formula IV is preferably carried out in the presence of an acid binding agent, particularly triethylamine or pyridine. Suitable solvents include chloroform, pyridine or dimethyl formamide. Usually the reaction temperature is between 0° C. and the boiling point of the reaction mixture.

The compounds of formula III in which $R_3$ is hydroxy, may be prepared by hydrolysis of the corresponding compounds in which $R_3$ is acyloxy.

The compounds of formula III can also be prepared by reaction of a benzomorphan of formula IV with a carboxylic acid of formula X

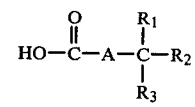

(X)

in which $R_1$-$R_3$ are as defined above, in the presence of dicyclohexylcarbodiimide. This acylation method is effected under normal conditions, e.g. in chloroform as a solvent, after which the reaction product is isolated in a conventional manner.

If a benzomorphan of formula IV, in which $R_5$ is hydroxy, is used as a starting compound, the hydroxy may be acylated as well, giving a compound of formula III in which $R_5$ is acyloxy, which however will be reduced again to hydroxy in the next reaction step.

Method A is advantageous for the preparation of compounds of formula I in which $R_3$ is alkoxy.

The preparation of the benzomorphans of formula IV is described in Dutch Patent Application Nos. 69.08527, 69.08528 and 76.01924. The compounds of formula IX and X are either known or may be produced in manner analogous to the production of known compounds.

In method B, the reaction is preferably carried out by using an equivalent amount or a small excess of the alkylation agent of formula V. Suitably an acid binding agent is used which does not react with the alkylation agent. For this purpose sterically hindered amines, e.g. dicyclohexylethylamine can be used, but generally inorganic bases such as sodium or potassium carbonate and especially sodium or potassium bicarbonate are preferred.

The reaction is preferably carried out in an inert organic solvent, e.g. acetone, butanone, tetrahydrofuran, dimethylformamide, dimethylsulphoxide, dioxane or methylene chloride or a mixture of such solvents. Tetrahydrofuran or dimethylformamide or mixtures thereof are preferred. Generally the reaction may be run from 0° C. to the boiling point of the solvent.

With less reactive alkylating agents the reaction can be accelerated by addition of catalytic or equivalent amounts of sodium or potassium iodide.

Method C is suitably carried out in an inert organic solvent, preferably a lower alcohol of 1–5 carbon atoms or in a mixture of such an alcohol with dichloromethane. Sometimes it is advantageous to add water to the reaction mixture.

The reaction conditions mainly depend on the reactivity of the epoxide. Usually the reaction may be run some hours and is preferably effected at temperatures in the range of 20°–120° C. Where a volatile epoxide is used, a closed system may be necessary.

Method D may be effected in an inert solvent immiscible with water, e.g. toluene, under conventional reaction conditions. Preferably the reaction is carried out in boiling toluene, with removal of the water which is formed. This method is preferably applied to compounds in which $R_3$ is other than hydroxy.

The reduction in method E may be effected in several ways. Preferably a hydride, e.g. lithium aluminium hydride, is used as a reducing agent, as described under method A. Reduction of carbonyl compounds to secondary alcohols of formula I can also be effected by catalytic hydrogenation. This hydrogenation is preferably carried out with platinium or palladium (optionally on charcoal) as a catalyst in a solvent such as methanol, ethanol or acetic acid or with Raney-nickel as a catalyst in ethanol.

The starting compounds of formula VIII may be prepared by alkylating a benzomorphan of formula IV with a compound of formula XI

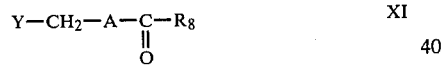

in which Y is halogen and A and $R_8$ are as defined above, in a manner described under method B.

The compounds of formula VIII, in which $R_8$ is alkyl may also be prepared by reaction of the corresponding carboxylic acid, carboxamide or carbonitrile with a suitable organometallic compound of formula $R_8M$, in which M is as defined above, in conventional manner.

Method F is carried out by conventional techniques, preferably in an inert solvent, such as tetrahydrofuran or diethylether and in a nitrogen atmosphere.

In method G, if two hydroxy groups are to be converted to alkoxy, hydroxy is suitably first converted into the corresponding alkali salt, e.g. with sodium hydride in an aprotic solvent. This salt is then treated with an alkyl halide or an alkyl or aryl sulphonic ester, preferably with an alkyl halide.

Due to the difference in acidity of the hydroxy radicals $R_3$ and $R_5$, $R_5$ may be alkylated selectively, e.g. by converting the hydroxy radical $R_5$ with dilute alkali hydroxide solution into an alkali salt and treating the product with a dialkyl sulphate.

The application of method H is preferably carried out with an acid chloride or anhydride as described under method A. A 2′-OH-group may be acylated selectively if an $R_3$=OH group is sterically hindered.

Suitable ether-cleaving reagents for method I include hydrogen halides e.g. hydrobromic acid and Lewis acids, e.g. boron tribromide. Aromatic ether groups may be cleaved selectively by sodium thioethoxide.

The hydrolysis of method J may be carried out under acid or alkaline conditions, preferably in aqueous alcoholic solution. An acyloxy group in the $R_5$ position can be hydrolysed selectively under mild conditions.

The starting materials of formulae V, VI, VII and XI are either known or may be prepared in conventional manner from known compounds.

The reaction products from any of methods A–J may be isolated from the reaction mixture and purified by conventional means.

Diastereoisomers may be separated by known techniques, based on their different physical and chemical characteristics, e.g. by fractional crystallisation or by column chromatography. These isomer separations may be effected after the final step of the synthesis or optionally in an earlier phase, after the formation of the mixture of stereoisomers. In cases in which in compounds of formula I, $R_3$ is alkoxy or acyloxy, the diastereoisomers of the corresponding hydroxyl compounds are suitably first separated by chromatography. Thereafter each separate isomer is alkylated or acylated.

Racemic mixtures may be resolved into their optical isomers, e.g. by separation of their salts with suitable optical active acids, in conventional manner.

The free base and acid addition salt forms of the compounds of formula I may be interconverted by standard methods.

The compounds of formula I possess pharmacological activity. In particular they possess analgetic and morphineantagonist activity, and are therefore indicated for use as analgetics and morphine antagonists, as indicated by (1) the tail retraction test in male Wistar rats, as described in Arzneim. Forsch. 13 502 (1963), the measuring times of 15 seconds being reduced to 10 seconds. The results may be evaluated according to the following three pain-killing levels:
  (a) moderate pain killing activity (M.A.): retraction time of the tail is between 6 and 10 seconds,
  (b) pronounced pain killing activity (P.A.): no retraction within 10 seconds, but a slight motion of the tail in warm water.
  (c) surgical pain killing activity (S.A.): no retraction within 10 seconds and no motion of the tail.

(2) the nalorfine activity test in the rat:
  0.63 mg fentanyl/kg body weight is administered s.c. to male Wistar rats to cause respiration depression, loss of righting reflex, muscle stiffening, killing of surgical pain and blocking of the cornea and pinna-reflexes. The ability to counteract these phenomena is a measure of the nalorfine activity of the compounds to be investigated. 30 Minutes after the s.c. injection, the animals are injected intravenously with the test compounds or with pentazocine and nalorfine as controls.

(3) the writhing test in the rat:
  1 ml 1% acetic acid is administered i.p. to female Wistar rats having a body weight of 150–190 g. During the following 25 minutes the number of writhings are noted. The average number of writhings is taken to 100 in control animals. The test compounds and the reference compounds are administered before the acetic acid injection, 30 minutes before, if subcutaneously and 45 minutes, if orally administered.

An indicated suitable daily dosage is from 0.1 to 100 mg, preferably administered in divided dosages of from 0.025 to 50 mg 2 to 4 times daily, or in retard form.

The compounds may be administered in free base form or in the form of their pharmaceutically acceptable acid addition salt forms, which salt forms have the same order of activity as the free base forms.

The compounds of formula I may be admixed with conventional pharmaceutically acceptable diluents or carriers and, optionally, other excipients, and administered for example in such forms as tablets, capsules and injectable solutions. They may be administered in combination preparations with other analgetics or with other active agents, e.g. sedatives, tranquillizers or hypnotics.

The following Examples illustrate the invention.

EXAMPLE 1

(Method A)

9,9-Dimethyl-5-ethyl-2'-hydroxy-2-(2-methoxyethyl)-6,7-benzomorphan hydrochloride To a solution of 3.0 g (12.3 mole) of 9,9-dimethyl-5-ethyl-2'-hydroxy-6,7-benzomorphan in 45 ml of dry methylene dichloride and 26.8 ml of triethylamine is added dropwise a solution of 4.0 g (36.6 mole) of methoxyacetyl chloride in 30 ml of dry methylene dichloride at room temperature.

The mixture is refluxed for 30 minutes. After cooling water is added, and the organic phase is separated from the aqueous phase, dried over magnesium sulphate and evaporated in vacuo. The mixture is filtered through a silica gel column with a mixture of cyclohexane and acetone (3:1) as the eluent. The fraction containing 9,9-dimethyl-5-ethyl-2-(2-methoxyacetyl)-2'-(2-methoxyacetyloxy)-6,7-benzomorphan is evaporated to dryness, giving a yellow oily residue (4.3 g).

The residue is dissolved in 80 ml of dry tetrahydrofuran. The solution is added dropwise, under a nitrogen atmosphere to a stirred suspension of 1.47 g (39 mole) of lithium aluminium hydride in 30 ml dry tetrahydrofuran at room temperature. After stirring for 30 minutes, 18 ml of ethyl acetate is carefully added dropwise followed by 150 ml of a saturated solution of ammonium chloride. The precipitate formed is filtered and washed with chloroform. The aqueous phase is separated from the chloroform phase and extracted three times with chloroform. The collected chloroform layers are dried over magnesium sulphate and evaporated in vacuo. The obtained residue is converted into the HCl salt and crystallized from a mixture of methanol and ethyl acetate, yielding 2.4 g of the title compound (m.p. 222°–225° C. decomp.).

EXAMPLES 2–7

(Method A)

In the same manner, the following N-substituted benzomorphan derivatives are obtained, starting from the listed N-unsubstituted benzomorphan derivatives and the corresponding acid chlorides:

| Example No. | Starting compound | N—substituent | salt | m.p. (°C.) |
|---|---|---|---|---|
| 2 | A | —CH$_2$CH$_2$OCH$_2$CH$_3$ | HCl | 222–230 (decomp) |
| 3 | A | —CH$_2$CH$_2$OCH$_2$CH$_2$CH$_3$ | HCl | 205–206 |
| 4 | A | —CH$_2$CH$_2$OCH(CH$_3$)$_2$ | HCl | 187–188 |
| 5 | A | —CH$_2$CH$_2$CH$_2$OCH$_3$ | HCl | 205 (decomp.) |
| 6 | B | —CH$_2$CH$_2$OCH$_3$ | HCl | 197–200 (decomp) |
| 7 | C | —CH$_2$CH$_2$OCH$_3$ | HCl | 227–229 |

Starting compounds
A: 9,9-dimethyl-5-ethyl-2'-hydroxy-6,7-benzomorphan
B: 9,9-dimethyl-2'-hydroxy-6,7-benzomorphan
C: 2'-hydroxy-5,9,9-trimethyl-6,7-benzomorphan

EXAMPLE 8

(Method A)

2-(2-t-Butoxyethyl)-9,9-dimethyl-5-ethyl-2'-hydroxy-6,7-benzomorphan hydrochloride To a solution of 4.44 g (32.6 mmole) t-butoxy-acetic acid in 25 ml dry chloroform is added dropwise over 15 minutes, at room temperature and in a nitrogen atmosphere, a solution of 3.89 g (32.6 mmole) thionyl chloride in 25 ml dry chloroform. After 20 hours stirring a solution of 2.0 g (8.16 mmole) of 9,9-dimethyl-5-ethyl-2'-hydroxy-6,7-benzomorphan in 18 ml of triethylamine and 20 ml of dry chloroform is added dropwise to the mixture. After refluxing for 30 minutes, the reaction mixture is cooled and water is added. The aqueous layer is extracted twice with chloroform, after which the combined chloroform layers are dried over magnesium sulphate.

After evaporation of the solvent in vacuo, the residue is filtered through a silica gel column with a mixture of cyclohexane and acetone (3:1) as the eluent. The fraction containing 2-(2-t-butoxyacetyl)-2'-(2-t-butoxyacetyloxy)-9,9-dimethyl-5-ethyl-6,7-benzomorphan is evaporated to dryness, yielding 2.7 g oily residue.

This residue is dissolved in 25 ml of dry tetrahydrofuran, and the solution is added dropwise under nitrogen to a suspension of 0.69 g (18 mmole) of lithium aluminium hydride in 25 ml dry of dry tetrahydrofuran at room temperature. After stirring for 30 minutes at room temperature 15 ml of ethyl acetate and 150 ml of a saturated ammonium chloride solution are carefully added dropwise. The precipitate formed is filtered and washed with chloroform. The aqueous layer is separated from the chloroform layer and extracted three times with chloroform. The collected chloroform layers are dried over magnesium sulphate and evaporated in vacuo. The residue is converted into the HCl salt and crystallized from a mixture of methanol and ethyl acetate. The yield of the title compound is 1.7 g, m.p. 196°–198° C.

EXAMPLES 9–21

(Method A)

Starting from the following N-unsubstituted benzomorphan derivatives and the corresponding carboxylic acids, N-substituted benzomorphan derivatives are obtained in the same manner as in Example 8.

| Example No. | Starting compound | N—substituent | salt | m.p. (°C.) |
|---|---|---|---|---|
| 9 | A | —CH$_2$CH$_2$CH$_2$OCH$_2$CH$_3$ | HCl | 170-172 (decomp.) |
| 10 | A | —CH$_2$CH(OCH$_3$)CH$_3$ | HCl | 235-238 |
| 11 | A | —CH$_2$CH(OC$_2$H$_5$)CH$_3$ | HCl | 233 (decomp.) |
| 12 | A | —CH$_2$C(CH$_3$)$_2$OCH$_3$ | HCl | 195-198 |
| 13 | A | —CH$_2$CH(OCH$_3$)CH$_2$CH$_3$ | HCl | 228-229 |
| 14 | B | —CH$_2$CH$_2$OCH$_2$CH$_3$ | HCl | 202-204 (decomp.) |
| 15 | B | —CH$_2$CH(OCH$_3$)CH$_3$ | HCl | 224-226 |
| 16 | C | —CH$_2$CH$_2$OCH$_2$CH$_3$ | HCl | 208-211 |
| 17 | C | —CH$_2$CH$_2$CH$_2$OCH$_3$ | HBr | 210-212 |
| 18 | C | —CH$_2$CH(OCH$_3$)CH$_3$ | HCl | 244-248 |
| 19 | D | —CH$_2$CH(OCH$_3$)CH$_3$ | HCl | 249-253 |
| 20 | E | —CH$_2$CH$_2$OCH$_3$ | HCl | 244-252 |
| 21 | E | —CH$_2$CH(OCH$_3$)CH$_3$ | HCl | 257-266* |

*Both diastereoisomers are separated by fractional crystallization. M.p. of isomer A 247-253° C. and of isomer B 262-267° C.

Starting compounds
A: 9,9-dimethyl-5-ethyl-2'-hydroxy-6,7-benzomorphan
B: 9,9-dimethyl-2'-hydroxy-6,7-benzomorphan
C: 2'-hydroxy-5,9,9-trimethyl-6,7-benzomorphan
D: 9,9-dimethyl-2'-hydroxy-5-n-propyl-6,7-benzomorphan
E: 9,9-dimethyl-5-phenyl-2'-hydroxy-6,7-benzomorphan

EXAMPLE 22

(Method A)

In the same manner as described in Example 1, but using pyridine instead of methylene dichloride/triethylamine as a solvent and refluxing for 1 hour instead of 30 minutes, the intermediate product 9,9-dimethyl-2-(2-methoxyacetyl)-2'-(2-methoxyacetyloxy)-6,7-benzomorphan is prepared, starting from 0.9 g of 9,9-dimethyl-2'-hydroxy-6,7-benzomorphan in 15 ml pyridine and 0.8 g of methoxyacetyl chloride in 5 ml of pyridine. The yield of the intermediate product is 1.5 g (yellow oil). The benzomorphan mentioned in Example 6 is obtained by reduction in the same way as described in Example 1.

EXAMPLE 23

(Method B)

9,9-Dimethyl-5-ethyl-2'-hydroxy-2-(2-hydroxyethyl)-6,7-benzomorphan hydrochloride To a mixture of 2.0 g (8.16 mmole) of 9,9-dimethyl-5-ethyl-2'-hydroxy-6,7-benzomorphan and 2.4 g of potassium bicarbonate in 12 ml of dry tetrahydrofuran is added, dropwise, a solution of 1.12 g (9 mmole) 2-bromoethanol in 5 ml of dry dimethylformamide. The reaction mixture is heated at 70° C. until complete conversion is determined by thin layer chromatography (~20 hr).

The reaction mixture is poured into water and extracted three times with chloroform. The collected chloroform layers are dried over magnesium sulphate and the solvent is evaporated in vacuo. The residue is then filtered over silica gel with toluene ethyl acetate as eluent (gradient elution). The fractions containing the desired compound are evaporated to dryness. The residue is converted into the HCl salt and crystallized from a mixture of methanol and ether. The yield of the obtained title compound amounts to 0.56 g, m.p. 227°-231° C.

EXAMPLE 24

Intermediates I 1-I 4 (Method B)

Using the following N-substituted benzomorphan derivatives and alkylating them with the compounds RX, N-substituted compounds are obtained in the same manner:

| Example No. | Starting compound | N—substituent (=R of the compound RX) | X (of RX) | salt | m.p. (°C.) |
|---|---|---|---|---|---|
| 24 | A | —CH$_2$CH$_2$OCH=CH$_2$ | Cl | — | oil |
| I 1 | D | —CH$_2$COOCH$_2$CH$_3$ | Br | — | — |
| I 2 | A | —CH$_2$C(O)CH$_3$ | Br | — | — |
| I 3 | A | —CH$_2$COOCH$_2$CH$_3$ | Br | — | — |
| I 4 | C | —CH$_2$COOCH$_2$CH$_3$ | Br | — | — |

The intermediate compounds I 1-I 4 were used for further reactions without purification.

The starting compounds A, C and D are as given under Examples 9-21.

EXAMPLE 25

(Method C)

9,9-Dimethyl-5-ethyl-2'-hydroxy-2-(1-hydroxycylopropylmethyl)-6,7-benzomorphan hydrochloride To a solution of 130 g (0.43 mole) 9,9-dimethyl-5-ethyl-2'-hydroxy-6,7-benzomorphan (containing 15% by wt. isopropanol) in 1 l absolute ethanol is added a solution of 40.4 g (0.57 mole) oxaspiropentane in 2825 g methylene chloride. After refluxing for 3 hours and cooling to room temperature, the solution is made weakly acid by adding isopropanol/HCl.

The solution is decolorised with activated charcoal and the solvent evaporated in vacuo. The residue is dissolved in 3 l boiling methanol, and as methanol is distilled from the boiling solution, ethyl acetate is added at a rate sufficient to maintain constant volume until crystallisation occurs. The crystalline product (112 g) is recrystallised from methanol/ethyl acetate to give the pure title product, m.p. 246°-249° C.

The compound of Example 25 may be prepared as its optical isomers, of which the (+) isomer has m.p. 242°-246° C., $\alpha_D$=+107.1° and the (−) isomer has m.p. 243°-247° C., $\alpha_D$=−108.8°, by using optically active starting material.

EXAMPLES 26-45

(Method C)

In manner analogous to Example 23, but using a closed reaction vessel where the epoxide used has a low boiling point, the following compounds are obtained:

| Example No. | Starting Compound | N—substituent | salt | m.p. (°C.) |
|---|---|---|---|---|
| 26 | A | —CH$_2$CHOHCH$_3$ | HCl | 226-229[2] / 215-220[3] |
| 27 | A | —CH$_2$C(CH$_3$)$_2$OH | HCl | 230-234 |
| 28 | A | —CH$_2$CHOHCH$_2$OCH$_3$ | HCl | 168-171[1] / 172-175[2] |
| 29 | A | —CH$_2$CHOHCH$_2$CH$_3$ | HCl | 235-238 |

-continued

| Example No. | Starting Compound | N—substituent | salt | m.p. (°C.) |
|---|---|---|---|---|
| 30 | A | —CH₂-(cyclobutyl-OH) | HCl | 259–268 |
| 31 | B | —CH₂C(CH₃)₂OH | HCl | 222–224 |
| 32 | B | —CH₂CHOHCH₂OCH₃ | — | — |
| 33 | C | —CH₂C(CH₃)₂OH | HCl | 239–241 |
| 34 | E | —CH₂C(CH₃)₂OH | HCl | 196–201 |
| 35 | E | —CH₂CHOHCH₂OCH₃ | — | — |
| 36 | E | —CH₂CHOHCH₃ | (COOH)₂ / HCl | 157–162⁽²⁾ / 261–266⁽³⁾ |
| 37 | E | —CH₂-(cyclobutyl-OH) | HCl | 243–253 |
| 38 | E | —CH₂-(cyclopropyl-OH) | (COOH)₂ | 165–172 |
| 39 | B | " | HCl | 250–254 |
| 40 | C | " | HCl | 247–251 |
| 41 | D | " | HCl | 216–219 |
| 42 | F | " | HCl | 203–205 |
| 43 | B | —CH₂-(cyclobutyl-OH) | HCl | 265 (dec.) |
| 44 | A | —CH₂-(cyclopentyl-OH) | HCl | 248–252 |
| 45 | A | —CH₂-(tetrahydropyranyl-OH) | HCl | 251–255 |

⁽¹⁾Isomers A + B
⁽²⁾Isomer A
⁽³⁾Isomer B

Starting materials A–E are as given above: starting material F is 9,9-dimethyl-5-ethyl-6,7-benzomorphan.

The compounds of Examples 32 and 35 were immediately used, in unpurified state, for further reactions.

EXAMPLE 46

(Method D)

9,9-Dimethyl-5-ethyl-2'-hydroxy-2-(2-methoxyethyl)-6,7-benzomorphan hydrochloride (Compound of Example 1)

A mixture of 2.0 g (8.16 mmole) of 9,9-dimethyl-5-ethyl-2'-hydroxy-6,7-benzomorphan, 0.62 g (8.16 mmole) 2-methoxyethanol and 1.7 g Raney nickel in 100 ml of dry toluene is refluxed for 48 hours under nitrogen. The water which is formed is removed by a Dean-Stark trap. After cooling the reaction mixture, the Raney nickel is separated by filtration and the filtrate is evaporated to dryness. The residue is filtered through silica gel (50 g) with toluene/ethyl acetate (8:2) as the eluent. The fraction containing the desired compound is evaporated to dryness in vacuo and the residue (0.7 g) is converted into the HCl salt and crystallised from methanol/ethyl acetate to obtain 420 mg of the title compound, m.p. 222°–226° C.

EXAMPLE 47

(Method E)

9,9-Dimethyl-5-ethyl-2'-hydroxy-2-(2-hydroxyethyl)-6,7-benzomorphan hydrochloride (Compound of Example 23)

800 mg of the unpurified intermediate product I 3 (an oil) is dissolved in 25 ml of dry tetrahydrofuran. The solution is added, dropwise and under nitrogen, to a suspension of 500 mg of lithium aluminium hydride in 10 ml of dry tetrahydrofuran. After 45 minutes stirring at room temperature, the excess lithium aluminium hydride is destroyed with ethyl acetate. Then 100 ml of a saturated solution of ammonium chloride are added dropwise. The formed precipitate is filtered and washed with chloroform. The water phase is separated from the chloroform phase and extracted three times with chloroform. The collected chloroform layers are dried over magnesium sulphate and evaporated to dryness in vacuo. The residue is converted into the HCl salt and crystallized in a mixture of methanol and ethyl acetate to obtain 350 mg of the title compound with m.p. 227°–230° C.

EXAMPLE 48

(Method F)

9,9-Dimethyl-5-ethyl-2'-hydroxy-2-(2-hydroxy-2-methyl-3-butenyl)-6,7-benzomorphan hydrochloride To a Grignard solution prepared from 1.68 g (70 mmole) of magnesium and 10.1 g (75 mmole) of vinyl bromide in 100 ml of tetrahydrofuran are added dropwise 8 g (26 mmole) of 9,9-dimethyl-5-ethyl-2'-hydroxy-2-(2-oxopropyl)-6,7-benzomorphan (compound I 2) in 80 ml dry tetrahydrofuran. After refluxing for 1 hour, a saturated ammonium chloride solution is added to destroy the excess of Grignard reagent. The tetrahydrofuran is evaporated in vacuo and to the residue concentrated ammonia is added. The basic mixture is extracted three times with toluene. The collected toluene layers are washed with water, dried over magnesium sulphate and concentrated in vacuo. After filtration through a silica gel column with methanol/chloroform (1:19) as the eluent, the fractions with the desired compound are evaporated to dryness in vacuo and converted into the HCl salt. After three recrystallisations from methanol/ethyl acetate 1.5 g of the pure title compound, being the less polar isomer (A) with m.p. 230°–236° C. (decomp.), are obtained. The more polar isomer (B) cannot be isolated in a pure state from the mother liquor. The ratio of the isomers A:B is about 9:1.

EXAMPLE 49

(Method F)

Using ethyl magnesium bromide instead of vinyl magnesium bromide is prepared in the same way 9,9-dimethyl-5-ethyl-5-ethyl-2'-hydroxy-2-(2-hydroxy-2- methylbutyl)-6,7-benzomorphan hydrochloride, m.p. 233°-235° C. (decomp.). The product is mainly a single isomeric form, as established by thin layer chromatography; probably the less polar A isomer

EXAMPLE 50

(Method F)

9,9-Dimethyl-5-ethyl-2'-hydroxy-2-(2-hydroxy-2-methyl-3-butynyl)-6,7-benzomorphan hydrochloride While stirring under a nitrogen atmosphere, purified acetylene is passed into 150 ml of dry, freshly distilled tetrahydrofuran during 45 minutes at −78° C. To this solution is added dropwise in 15 minutes 26.4 ml of a n-butyl lithium solution (1.5M in n-hexane) at the same temperature. After stirring for 10 minutes at −78° C. is added, dropwise, a solution of 6.0 g (17.8 mmole) of 9,9-dimethyl-5-ethyl-2'-hydroxy-2-(2-oxopropyl)-6,7-benzomorphan in 60 ml of dry tetrahydrofuran and stirring is continued for 30 min at −78° C. The reaction mixture is warmed to room temperature and water and a sodium bicarbonate solution are added. The organic phase is separated from the aqueous phase, washed with water, dried over magnesium sulphate and concentrated in vacuo. The residue (6.6 g) is a mixture of two isomers in a ratio of about 5:1. The mixture is converted into the HCl salt and crystallised from ethanol/ethyl acetate. After recrystallisation the isomers are obtained separately. Isomer A (less polar) has m.p. 203°-213° C., decomp., isomer B (more polar), m.p. 208°-216° C., decomp.

EXAMPLE 51

(Method F)

2-(2-Cyclopropyl-2-hydroxypropyl)-9,9-dimethyl-5-ethyl-2'-hydroxy-6,7-benzomorphan oxalate To a solution of 4.5 g (30 mmole) of cyclopropyl phenyl sulfide in 50 ml dry tetrahydrofuran is added dropwise, while stirring at 0° C. under nitrogen, 25 ml of a 2.3M solution of n-butyl lithium in n-hexane. After stirring for 2 hours at 0° C., a solution of 2.05 g (6.8 mmole) of 9,9-dimethyl-5-ethyl-2'-hydroxy-2-(2-oxopropyl)-6,7-benzomorphan in 50 ml dry tetrahydrofuran is added dropwise. Then the mixture is refluxed for 1 hour. After cooling, the organic layer is twice washed with water, dried over magnesium sulphate and concentrated in vacuo. The residue is filtered through a column of 100 g silica gel with cyclohexane/ether (3:1) as a eluent, to obtain 2 g of an adduct, which in order to remove the phenylmercapto group is boiled with 2 g Raney nickel in 100 ml of absolute ethanol. The completion of the reaction after 100 hours is established with thin layer chromatography. After filtration of the Raney nickel the filtrate is evaporated under reduced pressure and the residue is filtered through a silica gel column (100 g) with toluene/ethyl acetate (8:2) as the eluent. The obtained free base is converted into the oxalate with one equivalent of oxalic acid and crystallised from acetone. Yield 700 mg, m.p. 182°-186° C.

EXAMPLE 52

(Methods B and F)

9,9-Dimethyl-5-ethyl-2-(2-ethyl-2-hydroxybutyl)-2'-hydroxy-6,7-benzomorphan hydrochloride To a mixture of 5.0 g (20.4 mmole) of 9,9-dimethyl-5-ethyl-2'-hydroxy-6,7-benzomorphan and 4.04 g of potassium bicarbonate in 25 ml of dry tetrahydrofuran is added dropwise, while stirring under nitrogen, a solution of 4.2 g (25 mmole) of ethyl bromoacetate in 20 ml of dimethyl formamide. The reaction mixture is heated for 20 hours at 70° C. and after cooling is poured into water. The aqueous phase is extracted three times with chloroform. The collected chloroform extracts are dried over magnesium sulphate and are evaporated to dryness under reduced pressure to obtain 4.6 g of the crystalline free base.

1.0 g (3.0 mmole) of the base is redissolved in 20 ml of dry ether and the solution is added dropwise to a solution of 16 mmole ethyl magnesium iodide in 20 ml dry ether. After refluxing for 2 hours a saturated ammonium chloride solution is added dropwise. The aqueous layer is extracted with ether, the collected ether layers are dried over magnesium sulphate and evaporated to dryness under reduced pressure. The residue is filtered through a silica gel column with ether/petroleum as the eluant. The fractions containing the desired compound are evaporated to dryness under reduced pressure. The residue is converted into the HCl salt and crystallized from methanol/acetone to obtain 0.13 g of the title compound, m.p. 223°-233° C.

EXAMPLE 53

From the ethyl ester of the corresponding 5-propylbenzomorphan (intermediate I 1) and methyl magnesium iodide is obtained in the same manner as in Example 52 9,9-dimethyl-2'-hydroxy-(2-methyl-2-hydroxypropyl)-5-n-propyl-6,7-benzomorphan hydrochloride, m.p. 223°-226° C.

EXAMPLE 54

(Method G)

9,9-Dimethyl-5-ethyl-2'-methoxy-2-(2-methoxypropyl)-6,7-benzomorphan oxalate 1.7 ml (30 mmole) of methyl iodide and 0.93 g (20 mmole) of sodium hydride (55% suspension in oil) are added gradually to a solution of 1.0 g (3.15 mmole) of 9,9-dimethyl-5-ethyl-2'-hydroxy-2-(2-methoxypropyl)-6,7-benzomorphan in 4.5 ml of dry tetrahydrofuran, cooled to 0° C. The reaction mixture is stirred for 3 hours at room temperature. The excess of sodium hydride is carefully destroyed with water. After an acid-base separation and the evaporation of the organic phase to dryness under reduced pressure, the residue is converted into the oxalate and crystallised from acetone and from methanol/ethyl acetate to obtain 400 mg of the title compound, m.p. 157°-162° C.

EXAMPLE 55

(Method H)

9,9-Dimethyl-5-ethyl-2-(2-methoxypropyl)-2'-propionyloxy-6,7-benzomorphan oxalate A mixture of 1.5 g (4.7 mmole) 9,9-dimethyl-5-ethyl-2'-hydroxy-2-(2-methoxypropyl)-6,7-benzomorphan (Example 8), 3.0 g of 100% metaphosphoric acid and 12.0 g propionic anhydride is warmed at 50°-60° C. for 30 minutes while stirring. The reaction mixture is cooled and poured into water, concentrated ammonia is added to the water layer and the basic mixture is extracted with ethyl acetate. The collected ethyl acetate layers are dried over magnesium sulphate and evaporated to dryness under reduced pressure. The residue is converted into the oxalate and crystallised from methanol/ethyl acetate to obtain 0.99 g of the title compound, m.p. 129°–145° C.

EXAMPLE 56

(Method H)

2'-Benzoyloxy-9,9-dimethyl-5-ethyl-2-(2-hydroxy-2-methylpropyl)-6,7-benzomorphan hydrochloride 0.9 g (6.4 mmole) of benzoyl chloride in 10 ml of chloroform are added, dropwise under nitrogen and while stirring, to a solution of 1.54 g (4.85 mmole) of 9,9-dimethyl-5-ethyl-2'-hydroxy-2-(2-hydroxy-2-methylpropyl)-6,7-benzomorphan (Example 25) and 0.65 g (6.4 mmole) triethylamine in 20 ml dry chloroform. After stirring overnight at room temperature, the solution is refluxed for 6 hours. After cooling, water is added and an acid-base separation is effected. The base is converted into the HCl salt with isopropanol/HCl and crystallised from methanol/ethyl acetate to obtain 0.66 g of the title compound, m.p. 235°–239° C.

EXAMPLE 57

(Method I)

9,9-Dimethyl-5-ethyl-2'-hydroxy-2-(3-hydroxypropyl)-6,7-benzomorphan hydrochloride A solution of 1.06 ml (9.33 mmole) of boron tribromide in 15 ml of dry methylene dichloride is added dropwise, in 30 minutes, to a solution of 1.0 g (2.82 mmole) of 9,9-dimethyl-5-ethyl-2'-hydroxy-2-(3-methoxypropyl)6,7-benzomorphan hydrochloride (Example 27) in 28 ml of dry methylene dichloride. After stirring for 2½ hours at room temperature, water is carefully added, concentrated ammonia is added to the water layer and the basic mixture is extracted three times with chloroform. The collected chloroform layers are dried over magnesium sulphate and concentrated under reduced pressure. The residue is filtered through silica gel with cyclohexane/acetone (3:1) as the eluent. The fractions containing the desired compound are evaporated to dryness under reduced pressure. The residue is converted into the HCl salt and crystallised from methanol/ethyl acetate to obtain 560 mg of the title compound, m.p. 235°–239° C.

EXAMPLE 58

(Methods G and I)

9,9-Dimethyl-2'-hydroxy-2-(2-methoxy-2-methylpropyl)-6,7-benzomorphan hydrochloride Starting from 9,9-dimethyl-2'-hydroxy-2-(2-hydroxy-2-methylpropyl)-6,7-benzomorphan (Example 29), 9,9-dimethyl-2'-methoxy-2-(2-methoxy-2-methylpropyl)-6,7-benzomorphan hydrochloride, m.p. 187°–189° C. (decomp.) is prepared in manner analogous to Example 55.

To a stirred suspension of 24 mmole (1.2 g of a suspension in oil) of sodium hydride in 30 ml dry dimethylformamide are added dropwise at room temperature 3 ml (50 mmole) ethanethiol. After stirring for 30 minutes a solution of 532 mg (1.5 mmole) of 9,9-dimethyl-2'-methoxy-2-(2-methoxy-2-methylpropyl)-6,7-benzomorphan hydrochloride in 45 ml dry dimethylformamide is added dropwise. After refluxing for 3 hours the solvent is evaporated under reduced pressure and the residue is subjected to an acid-base separation. The free base is converted into the HCl salt and crystallised from methanol/isopropanol to obtain 210 mg of the title compound, m.p. 215°–216° C. (decomp.).

EXAMPLES 59–66

By methylation of the hydroxyl groups in position 2' and in the N-substituent of the benzomorphans mentioned in the following table, and conversion of the 2'-methoxy into a 2'-hydroxyl group in manner analogous to Example 56, corresponding compounds are prepared. In the table the numbers in the second column are the Example numbers of the starting compounds, and the N-substituents given are those of the final products. The other substituents of the compounds obtained are those in the starting compounds.

EXAMPLES 67, 68

In analogous manner, the compound of Example 27 may be di-ethylated or di-allylated and the 2'-ethoxy or alkyloxy group converted to a 2'-hydroxyl group to give the corresponding compounds as shown in the table:

| Example No. | Starting compound | N—substituent of the product | salt | m.p. (°C.) |
|---|---|---|---|---|
| 59[2] | 26[2] | —CH₂CH(OCH₃)CH₃ | HCl | 115 (decomp.) |
| 59[3] | 26[3] | —CH₂CH(OCH₃)CH₃ | HCl | 260 (decomp.) |
| 60 | 28 | —CH₂CH(OCH₃)CH₂OCH₃ | HCl | 196–199 |
| 61 | 25 | —CH₂—(cyclopropyl with OCH₃) | HCl | 246–252 |
| 62 | 30 | —CH₂—(cyclobutyl with OCH₃) | HCl | 253–260 |
| 63 | 32[1] | —CH₂CH(OCH₃)CH₂OCH₃ | HCl | 202–207 |
| 63[2] | 32[2] | " | HCl | 201–205 |
| 63[3] | 32[3] | " | HCl | 224–228 |
| 64 | 33 | —CH₂C(CH₃)₂OCH₃ | HCl | 195–198 |
| 65 | 35 | —CH₂CH(OCH₃)CH₂OCH₃ | HCl | 202–207 |
| 66 | 37 | —CH₂—(cyclopentyl with OCH₃) | HCl | 262–268 |
| 67 | 27 | —CH₂C(CH₃)₂OC₂H₅ | HCl | 200–203 |
| 68 | 27 | —CH₂C(CH₃)₂OCH₂CH=CH₂ | HCl | 195–198 |

[1] mixture of A- and B-isomers
[2] A-isomer
[3] B-isomer

EXAMPLE 69

(Methods H and J)

2-(2-Acetoxy-2-methylpropyl)9,9-dimethyl-5-ethyl-2'-hydroxy-6,7-benzomorphan hydrochloride A mixture of 1.25 g (4 mmole) 9,9-dimethyl-5-ethyl-2'-hydroxy-(2-hydroxy-2-methylpropyl)-6,7-benzomorphan (Example 25), 2.5 g metaphosphoric acid (100%) and 12 ml acetic anhydride is warmed at 60° C. for 30 minutes. After cooling, water is added carefully, and the solution is made alkaline and extracted with ethyl acetate, which is dried over magnesium sulphate and evaporated under reduced pressure. The compound is converted into the HCl salt and crystallised from methanol/ethyl acetate to obtain the diester, m.p. 180°–185° C.

The compound is dissolved in isopropanol and acidified with isopropanol-HCl, then refluxed for 3 hours to split off the phenolic acetoxy radical. After evaporation to dryness, the residue is crystallised from methanol/ethyl acetate, to obtain 0.32 g of the title compound, m.p. 170°–173° C.

EXAMPLES 70–76

By acylation of the hydroxyl groups in position 2' and in the N-substituent of the benzomorphans mentioned in the following table, followed by the conversion of the 2'-acyloxy into the 2'-hydroxyl group, corresponding compounds are prepared in manner analogous to that of Example 69. The acylation is effected by using the corresponding acid anhydride, with the exception of the benzoylation, which is carried out with benzoyl chloride. In the table the numbers in the second column are the Example numbers of the starting compounds and the N-substituents are those of the compounds obtained. The other substituents of the compounds obtained are those of the starting compounds:

| Example No. | Starting compound | N—substituent of the product | salt | m.p. (°C.) |
|---|---|---|---|---|
| 70 | 26[1] | —CH$_2$CH(CH$_3$)OOCCH$_3$ | HCl | 204–208 |
| 71[2] | 26[2] | —CH$_2$CH(CH$_3$)OOCC$_2$H$_5$ | HCl | 200–204 |
| 71[3] | 26[3] | —CH$_2$CH(CH$_3$)OOCC$_2$H$_5$ | HCl | 198–201 |
| 72[2] | 26[2] | —CH$_2$CH(CH$_3$)OOCC$_6$H$_5$ | HCl | 167–201 |
| 72[3] | 26[3] | —CH$_2$CH(CH$_3$)OOCC$_6$H$_5$ | HCl | 200–203 |
| 73 | 27 | —CH$_2$C(CH$_3$)$_2$OOCC$_2$H$_5$ | HCl | 170–171 |
| 74 | 27 | —CH$_2$C(CH$_3$)$_2$OOCnC$_3$H$_7$ | HCl | 195–200 |
| 75 | 27 | —CH$_2$C(CH$_3$)$_2$OOCiC$_3$H$_7$ | HCl | 182–185 |
| 76 | 33 | —CH$_2$C(CH$_3$)$_2$OOCC$_2$H$_5$ | HCl | 201–204 |

[1] A + B isomer
[2] A-isomer
[3] B-isomer

The following table gives pharmacological test results for the compounds of the Examples. In the tail retraction test, the figures given are ED$_{50}$ values in mg/kg body weight for subcutaneous administration, to give each of the three pain-killing levels described above. In the nalorfine activity test, the ED$_{50}$ (in mg/kg body weight) in the table was calculated from the ability to antagonise each of the four parameters, the average value being taken. In the writhing test the ED$_{50}$ (mg/kg) was calculated based on a half number of writhings.

Values for pentazocine and nalorfine are given for purposes of comparison.

TABLE

| Example No. | Tail retraction test | | | Nalorfine activity | writhing test | |
|---|---|---|---|---|---|---|
| | M.A. | P.A. | S.A. | | s.c. | p.o. |
| 1 | >2.2 | >2.2 | >2.2 | 0.0026 | 0.53 | 4.5 |
| 2 | >2.2 | >2.2 | >2.2 | 0.023 | 0.36 | 3.0 |
| 3 | >2.2 | >2.2 | >2.2 | 0.69 | 0.83 | >31.6 |
| 4 | 1.9 | >2.2 | >2.2 | 0.16 | 0.67 | 11.1 |
| 5 | >2.2 | >2.2 | >2.2 | 0.35 | 0.39 | 59.6 |
| 6 | >31.6 | >31.6 | >31.6 | 0.00038 | >31.6 | — |
| 7 | >2.2 | >2.2 | >2.2 | 0.0011 | 0.018 | 16.5 |
| 8 | >2.2 | >2.2 | >2.2 | 0.823 | >3.2 | >32 |
| 9 | >2.2 | >2.2 | >2.2 | 0.84 | >3.2 | >32 |
| 10 | 0.03 | 0.09 | 0.38 | >2.2 | 0.004 | ~3.2 |
| 11 | 0.147 | 0.68 | 1.9 | 1.13 | 0.14 | 17.8 |
| 12 | >2.2 | >2.2 | >2.2 | 0.41 | 0.085 | 13.1 |
| 13 | 0.26 | 0.62 | >2.2 | >2.2 | 0.07 | 8.5 |
| 14 | >2.2 | >2.2 | >2.2 | 0.015 | >3.2 | — |
| 15 | >2.2 | >2.2 | >2.2 | 0.066 | 0.028 | 3.6 |
| 16 | >2.2 | >2.2 | >2.2 | 0.055 | 0.49 | 1.34 |
| 17 | — | — | — | — | >3.2 | — |
| 18 | >2.2 | >2.2 | >2.2 | — | 0.24 | — |
| 19 | 0.24 | 0.50 | 1.50 | — | 0.083 | — |
| 20 | >2.2 | >2.2 | >2.2 | 0.048 | 0.93 | >32 |
| 21[2] | 0.26 | 0.91 | >2.2 | 0.91 | 0.034 | 1.6 |
| 21[3] | 1.78 | >2.2 | >2.2 | 0.97 | 0.90 | 10.5 |
| 23 | >2.2 | >2.2 | >2.2 | 0.453 | >3.2 | >32 |
| 25 | >2.2 | >2.2 | >2.2 | 0.03 | 0.01 | 0.46 |
| 26[1] | >2.2 | >2.2 | >2.2 | 0.0161 | 0.14 | 23.8 |
| 26[2] | 0.58 | >2.2 | >2.2 | 0.05 | 0.93 | 12.8 |
| 26[3] | 0.68 | >2.2 | >2.2 | 0.05 | 0.50 | 8.5 |
| 27 | >2.2 | >2.2 | >2.2 | 0.13 | 0.031 | 4.6 |
| 28[2] | 0.58 | 1.21 | >2.2 | 0.21 | 1.1 | — |
| 29 | >2.2 | >2.2 | >2.2 | 0.51 | 0.56 | 1.33 |
| 30 | >2.2 | >2.2 | >2.2 | 0.029 | 0.098 | 1.06 |
| 31 | >2.2 | >2.2 | >2.2 | 0.0015 | 0.064 | 5.14 |
| 33 | >2.2 | >2.2 | >2.2 | 0.058 | 0.035 | 7.7 |
| 34 | >2.2 | >2.2 | >2.2 | 4.28 | 0.63 | 9.1 |
| 36[2] | — | — | — | — | 0.86 | 11.8 |
| 36[3] | — | — | — | — | 1.1 | 29.7 |
| 37 | >2.2 | >2.2 | >2.2 | 0.67 | 0.028 | 2.69 |
| 38 | >2.2 | >2.2 | >2.2 | 0.46 | 0.32 | 2.9 |
| 39 | >2.2 | >2.2 | >2.2 | 0.052 | 0.042 | 2.69 |
| 40 | >2.2 | >2.2 | >2.2 | 0.035 | 0.017 | 2.96 |
| 41 | >2.2 | >2.2 | >2.2 | 0.049 | 0.015 | 3.23 |
| 43 | — | — | — | — | 0.0063 | 11.3 |
| 44 | 1.77 | — | — | 0.055 | 0.021 | 5.78 |

TABLE-continued

| Example No. | Tail retraction test M.A. | P.A. | S.A. | Nalorfine activity | writhing test s.c. | p.o. |
|---|---|---|---|---|---|---|
| 48 | — | — | — | — | 0.21 | — |
| 49 | >2.2 | >2.2 | >2.2 | 0.44 | 0.24 | 9.4 |
| 50[2] | 0.58 | >2.2 | >2.2 | 0.0008 | 0.88 | 10.4 |
| 50[3] | 0.15 | 1.47 | >2.2 | ≦0.06 | 0.009 | 2.34 |
| 51 | 0.068 | 0.41 | >0.46 | 0.125 | 0.087 | 23.8 |
| 52 | >2.2 | >2.2 | >2.2 | >2.2 | 1.22 | — |
| 53 | >2.2 | >2.2 | >2.2 | 0.67 | 0.20 | 8.47 |
| 54 | >2.2 | >2.2 | >2.2 | >2.2 | 0.13 | — |
| 55 | 0.26 | 0.68 | 1.62 | >2.2 | 0.017 | 9.8 |
| 56 | >2.2 | >2.2 | >2.2 | 0.77 | 0.22 | 31.6 |
| 58 | >2.2 | >2.2 | >2.2 | 0.082 | 0.45 | 13.1 |
| 59[2] | 0.026 | 0.068 | >0.46 | 0.015 | 0.002 | 4.0 |
| 59[3] | 1.08 | >2.2 | >2.2 | 0.78 | 0.29 | 12.7 |
| 60 | 0.056 | 0.23 | 0.56 | >2.2 | 0.015 | 10.8 |
| 61 | >2.2 | >2.2 | >2.2 | 0.57 | 0.96 | 1.06 |
| 62 | 0.91 | >2.2 | >2.2 | >2.2 | 0.28 | 10.2 |
| 63 | 0.026 | 0.15 | 0.91 | 0.91 | 0.05 | 3.4 |
| 64 | 0.37 | >2.2 | >2.2 | 0.28 | 0.039 | 9.1 |
| 65 | 0.13 | 0.37 | 0.93 | — | 1.72 | — |
| 66 | >2.2 | >2.2 | >2.2 | >2.2 | 1.7 | 10.2 |
| 67 | — | — | — | — | 1.40 | 5.07 |
| 68 | — | — | — | — | 2.50 | 4.7 |
| 69 | >2.2 | >2.2 | >2.2 | 0.406 | 0.25 | 11.0 |
| 70 | >2.2 | >2.2 | >2.2 | 0.37 | 0.91 | 5.2 |
| 71[2] | 1.78 | >2.2 | >2.2 | 0.30 | 1.4 | >32 |
| 71[3] | >2.2 | >2.2 | >2.2 | 0.34 | 0.64 | 31.0 |
| 73 | >2.2 | >2.2 | >2.2 | >2.2 | 0.17 | 3.3 |
| 74 | — | — | — | — | 0.7 | 14.1 |
| 75 | — | — | — | — | 1.2 | 6.2 |
| 76 | — | — | — | — | 0.8 | 10.4 |
| Pentazocine HCl | 14.7 | 53 | >100 | >2.2 | 5.6 | 278 |
| Nalorfine HBr | 18 | >22 | >22 | 0.16 | 6.6 | — |

[1] A + B isomer
[2] A isomer
[3] B isomer

What is claimed is:

1. A compound of formula I,

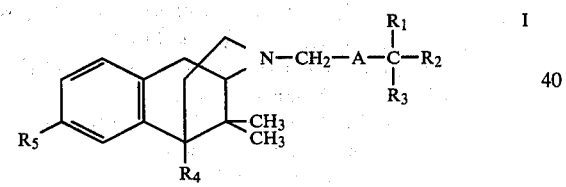

in which
A is a direct bond or —CH$_2$—,
R$_1$ is C$_{1-3}$alkyl, C$_{2-3}$alkenyl, C$_{2-3}$alkynyl, C$_{1-2}$alkoxy C$_{1-2}$alkyl or C$_{3-6}$cycloalkyl,
R$_2$ is hydrogen or C$_{1-3}$alkyl, or
R$_1$ and R$_2$, together with the carbon atom to which they are attached, form a C$_{3-6}$cycloalkyl group or a 4 to 6-membered heterocycloalkyl group containing one oxygen atom as the sole hetero atom,
R$_3$ is hydroxy, C$_{1-4}$alkoxy, C$_{2-4}$alkenyloxy, or R$_6$COO- in which R$_6$ is hydrogen, C$_{1-3}$alkyl, phenyl or benzyl,
R$_4$ is hydrogen, C$_{1-4}$alkyl or phenyl, and
R$_5$ is hydrogen, hydroxy, C$_{1-3}$alkoxy or R$_7$COO- where R$_7$ is hydrogen, C$_{1-3}$alkyl, phenyl, benzyl, phenethyl or 3-pyridyl, or a pharmaceutically acceptable acid addition salt form thereof in optically active or racemic mixture form.

2. A compound according to claim 1 in which R$_5$ is hydroxy.

3. A compound according to claim 2 in which A is a direct bond.

4. A compound according to claim 1 of formula Ia

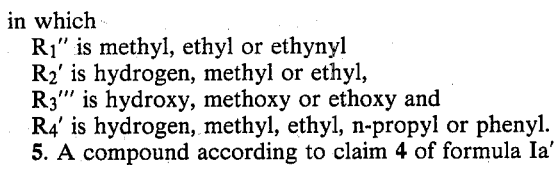

in which
R$_1''$ is methyl, ethyl or ethynyl
R$_2'$ is hydrogen, methyl or ethyl,
R$_3'''$ is hydroxy, methoxy or ethoxy and
R$_4'$ is hydrogen, methyl, ethyl, n-propyl or phenyl.

5. A compound according to claim 4 of formula Ia'

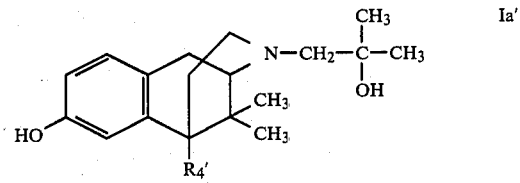

in which R$_4'$ is as defined in claim 4.

6. A compound according to claim 1 of formula Ib

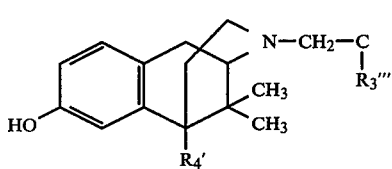

in which Z is —CH₂—CH₂—, —CH₂—₃ or—CH₂—₄ and R₃''' and R₄' are as defined in claim 4.

7. A compound according to claim 6 of formula Ib'

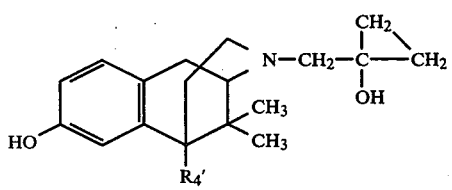

in which R₄' is as defined in claim 4.

8. A compound according to claim 1 in which R₁ is C$_{1-3}$alkyl, R₂ is hydrogen or C$_{1-3}$alkyl, or R₁ and R₂, together with the carbon atom to which they are attached, form a C$_{3-6}$cycloalkyl group; R₃ is hydroxy or C$_{1-4}$alkoxy; R₄ is hydrogen, methyl, ethyl or n-propyl; and R₅ is hydroxy; or a pharmaceutically acceptable acid addition salt thereof in optically active or racemic form.

9. A compound according to claim 8 in which R₁ is methyl, R₂ is hydrogen or methyl, or R₁ and R₂, together with the carbon atom to which they are attached, form a cyclopropyl or cyclobutyl group; R₃ is hydroxy, methoxy or ethoxy; R₄ is hydrogen, methyl, ethyl or n-propyl; and R₅ is hydroxy; or a pharmaceutically acceptable acid addition salt thereof in optically active or racemic form.

10. A compound according to claim 1, in which A is a direct bond.

11. The compound of claim 1 which is 9,9-dimethyl-5-ethyl-2'-hydroxy-2-(1-hydroxycyclopropylmethyl)-6,7-benzomorphan.

12. The compound of claim 1 which is (+)-9,9-dimethyl-5-ethyl-2'-hydroxy-2-(1-hydroxycyclopropylmethyl)-6,7-benzomorphan.

13. The compound of claim 1 which is (−)-9,9-dimethyl-5-ethyl-2'-hydroxy-2-(1-hydroxycyclopropylmethyl)-6,7-benzomorphan.

14. A compound of claim 1 in which A is a direct bond and R₁, R₂, R₃, R₄ and R₅ are respectively: (a) CH₃, CH₃, OH, C₂H₅ and OH or (b) CH₃, CH₃, OH, CH₃ and OH.

15. A compound of claim 1 in which A is a direct bond, R₁ and R₂ together with the carbon atom to which they are attached is cyclopropyl and R₃, R₄ and R₅ are respectively: (a) OH, phenyl and OH; (b) OH, H and OH or (c) OH, CH₃ and OH.

16. A compound of claim 1 selected from the group consisting of:
(a) 9,9-dimethyl-5-ethyl-2'-hydroxy-2-(2-hydroxy-2-methyl-3-butenyl)-6,7-benzomorphan;
(b) 9,9-dimethyl-5-ethyl-2'-hydroxy-2-(2-hydroxy-2-methyl-3-butynyl)-6,7-benzomorphan;
(c) 2-(2-acetoxy-2-methylpropyl)-9,9-dimethyl-5-ethyl-2'-hydroxy-6,7-benzomorphan;
(d) 9,9-dimethyl-5-phenyl-2'-hydroxy-2-(1-hydroxycyclobutylmethyl)-6,7-benzomorphan;
(e) 9,9-dimethyl-5-ethyl-5'-hydroxy-5-(4-hydroxy-4-tetrahydropranylmethyl)-6,7-benzomorphan; and
(f) 9,9-dimethyl-5-ethyl-2'-hydroxy-2-(1-methoxycyclopropylmethyl)-6,7-benzomorphan.

17. A compound of claim 1 selected from the group consisting of:
(a) 9,9-dimethyl-2'-hydroxy-2-(2-hydroxy-2-methylpropyl)-6,7-benzomorphan and
(b) 9,9-dimethyl-5-phenyl-2'-hydroxy-2-(2-hydroxy-2-methylpropyl)-6,7-benzomorphan.

18. A compound of claim 1 selected from the group consisting of:
(a) 9,9-dimethyl-2'-hydroxy-5-n-propyl-2-(1-hydroxycyclopropylmethyl)-6,7-benzomorphan and
(b) 9,9-dimethyl-5-ethyl-2-(1-hydroxycyclopropylmethyl)-6,7-benzomorphan.

19. A compound of claim 1 selected from the group consisting of:
(a) 9,9-dimethyl-5-ethyl-2'-hydroxy-2-(1-hydroxycyclobutylmethyl)-6,7-benzomorphan;
(b) 9,9-dimethyl-2'-hydroxy-2-(1-hydroxycyclobutylmethyl)-6,7-benzomorphan and
(c) 9,9-dimethyl-5-ethyl-5'-hydroxy-5-(1-hydroxycyclopentylmethyl)-6,7-benzomorphan.

20. A compound of claim 1 selected from the group consisting of:
(a) 9,9-dimethyl-5-ethyl-2'-hydroxy-2-(2-methoxy-2-methylpropyl)-6,7-benzomorphan and
(b) 2'-hydroxy-5,9,9-trimethyl-2-(2-methoxy-2-methylpropyl)-6,7-benzomorphan.

21. A compound of claim 1 selected from the group consisting of:
(a) 9,9-dimethyl-5-ethyl-2'-hydroxy-2-(2-methoxypropyl)-6,7-benzomorphan;
(b) 9,9-dimethyl-5-phenyl-2'-hydroxy-2-(2-methoxypropyl)-6,7-benzomorphan;
(c) 9,9-dimethyl-5-ethyl-2'-hydroxy-2-(2-hydroxypropyl)-6,7-benzomorphan;
(d) 9,9-dimethyl-5-ethyl-2'-hydroxy-2-(2-hydroxybutyl)-6,7-benzomorphan and
(e) 9,9-dimethyl-5-phenyl-2'-hydroxy-2-(2-hydroxypropyl)-6,7-benzomorphan.

22. A compound of claim 1 selected from the group consisting of:
(a) 9,9-dimethyl-5-ethyl-2'-hydroxy-2-(2-hydroxy-3-methoxypropyl)-6,7-benzomorphan;
(b) 9,9-dimethyl-2'-hydroxy-2-(2-hydroxy-3-methoxypropyl)-6,7-benzomorphan and
(c) 9,9-dimethyl-5-phenyl-2'-hydroxy-2-(2-hydroxy-3-methoxypropyl)-6,7-benzomorphan.

23. A compound of formula:

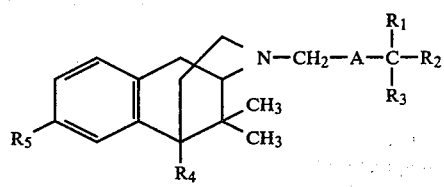

in which
A is a direct bond;
R₁ is hydrogen;
R₂ is hydrogen or C$_{1-3}$alkyl;
R₃ is ethoxy;

$R_4$ is hydrogen, $C_{1-4}$alkyl or phenyl; and
$R_5$ is hydrogen, hydroxy, $C_{1-3}$alkoxy or $R_7$COO- where $R_7$ is hydrogen, $C_{1-3}$alkyl, phenyl, benzyl, phenethyl or 3-pyridyl;
or a pharmaceutically acceptable acid addition salt thereof in optically active or racemic form.

24. A compound according to claim 23 in which $R_4$ is hydrogen or methyl, ethyl or n-propyl; and $R_5$ is hydroxy.

25. A compound according to claim 24 in which $R_2$ is hydrogen or methyl; and $R_4$ is hydrogen, methyl, ethyl or n-propyl.

26. A compound of claim 23 selected from the group consisting of:

(a) 9,9-dimethyl-5-ethyl-2'-hydroxy-2-(2-ethoxyethyl)-6,7-benzomorphan and (b) 2'-hydroxy-5,9,9-trimethyl-2-(2-ethoxyethyl)-6,7-benzomorphan.

27. A pharmaceutical composition useful in treating pain comprising a therapeutically effective amount of an optically active or racemic compound of formula I, stated in claim 1, or a pharmacologically acceptable acid addition salt thereof, in association with a pharmacologically acceptable diluent or carrier.

28. A method of pain-killing treatment of a mammal comprising administering an analgetically effective dose of a compound of formula I, stated in claim 1, or a pharmacologically acceptable acid addition salt thereof.

* * * * *